United States Patent [19]

Nakajima

[11] 4,345,590
[45] Aug. 24, 1982

[54] SUPPORT BANDAGE

[75] Inventor: Kikuo Nakajima, Kosai, Japan

[73] Assignee: Kuniaki Yamazaki, Chiba, Japan

[21] Appl. No.: 201,406

[22] PCT Filed: Feb. 26, 1980

[86] PCT No.: PCT/JP80/00026

§ 371 Date: Oct. 26, 1980

§ 102(e) Date: Oct. 23, 1980

[87] PCT Pub. No.: WO80/01758

PCT Pub. Date: Sep. 4, 1980

[51] Int. Cl.³ .............................................. A61F 13/06
[52] U.S. Cl. ................................................... 128/166
[58] Field of Search ................ 128/80 R, 80 H, 89 R, 128/153, 166, 166.5

[56] References Cited

U.S. PATENT DOCUMENTS

| 3,312,219 | 4/1967 | Peckham | 128/80 R |
| 3,989,041 | 11/1976 | Davies | 128/166 |
| 4,141,358 | 2/1979 | DeMarco | 128/166 |

*Primary Examiner*—C. Fred Rosenbaum
*Attorney, Agent, or Firm*—Koda and Androlia

[57] ABSTRACT

A support bandage, wherein at least three extended portions are connected to a foot sole attachable portion, out of said three extended portions, a first one is to be closely attached to the inner side of the body, a second one to be closely attached to the outer side of the body and a third one to be closely attached to the rear side of the leg, and all of said three extended portions are adhesively attached to the leg to thereby prevent a sprain of an ankle or the like for the protection thereof.

10 Claims, 11 Drawing Figures

SUPPORT BANDAGE

BACKGROUND OF THE INVENTION

1. Field of the Invention

The present invention relates to a support bandage being wound around a joint or like in a human body for preventing and curing a sprain and the like.

2. Description of the Prior Art

Heretofore, there has been known the so-called support bandage, i.e., winding an expandable tape or tapes around an ankle and the like before the start of a sport, whereby a sprain, torn muscle or damaged muscle are prevented, and curing the affected part as described above after an injury has occurred, thereby enabling to make the physical activity that follows possible.

Description will hereunder be given of a case where the support bandage is applied to prevent a sprain in an ankle with reference to FIGS. 1 and 2. Firstly, a tape 12 is wound around a portion adjacent a calf 10 by the utilization of the adhesion thereof. Next, one end 14A of the tape 14 is adhesively attached to the outer side of the body, and the intermediate portion 14B to a foot sole 16. In this case, a high tension is applied to a portion between one end 14A and the intermediate portion 14B to expand the tape 14, whereby the intermediate portion 14B is adhesively attached to the foot sole 16 (in a direction indicated by an arrow A). Thereafter, if the other end 14C of the tape 14 is adhesively attached to the tape 12 at the inner side of the body, then the taping operation is completed, and as necessary a plurality of tapes are adhesively attached in the same manner as the tape 14 and the tension is adjusted.

The tension of this tape 14 (in a direction indicated by the arrow A) makes it possible to reliably prevent an injury caused by the rotation of the joint of an ankle 18 toward the inner side of the body to an extreme extent (in a direction indicated by an arrow B), i.e., a sprain.

In addition to the above, taping is applicable to various joints, tendons, muscular portions so as to effectively prevent any possible injury or the like, and further, if taping may be applied after an injury, then the physical activity can be continued in spite of the occurrence of the injury such as a sprain, thus eliminating the necessity of using a walking stick or the like. Since taping has such high advantages as described above, some countries impose sportsmen an obligation to fasten taping to themselves.

However, with the taping having such outstanding advantages as described above, the applying methods are different in accordance with the types and parts of injury which would possibly occur or occurred. In order to fully obtain the advantages, it is necessary to attain high level of skill in applying the tapes and to obtain the help of specially trained persons such as sports trainers.

SUMMARY OF THE INVENTION

This invention has been developed to obtain the abovedescribed advantages, and has as its object the provision of a support bandage which can be easily fastened without requiring special level of skill and from which reliable advantages can be expected to be obtained.

A support bandage according to the present invention is formed of a continuous thin sheet material in which at least three extended portions are projected from a foot sole attaching portion thereof, a first portion out of the projected portions is to be closely attached to the inner side of the body, a second portion is to be closely attached to the outer side of the body and a third portion is to be closely attached to the rear of the foot, and the three portions as described above are adhesively attached to the foot, respectively, so as to be readily wound around the ankle.

Description will hereunder be given of the embodiments of the present invention with reference to the drawings.

DESCRIPTION OF THE PREFERRED EMBODIMENTS

Figure 1:
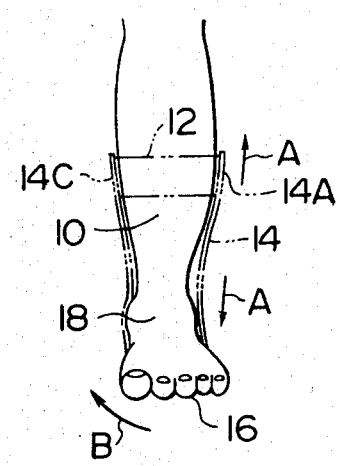
FIG. 1 is a front view showing the conventional taping method.
Figure 2:
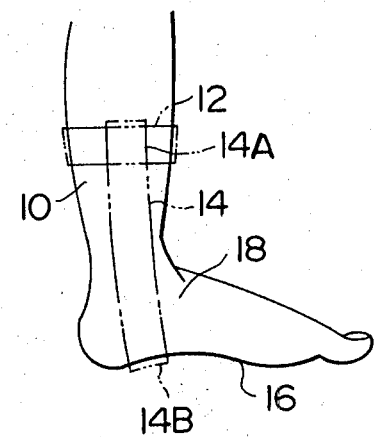
FIG. 2 is a side view of FIG. 1.
Figure 3:
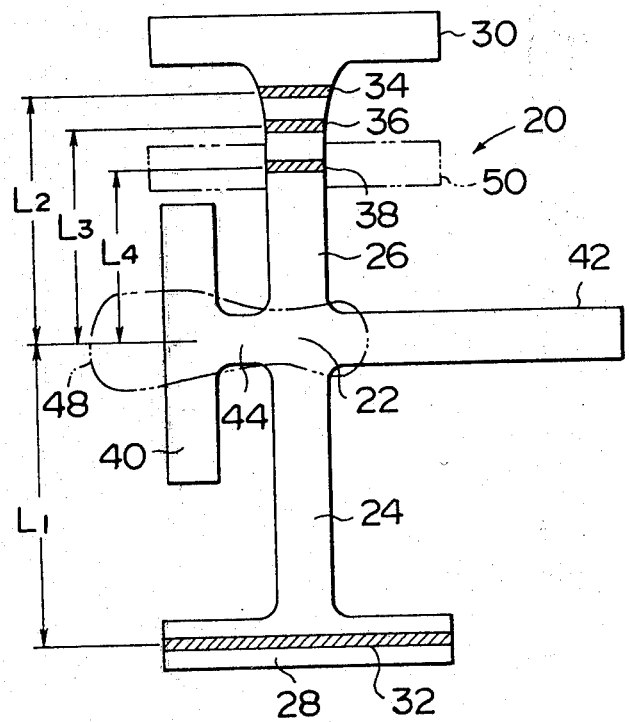
FIG. 3 is a bottom view showing a first embodiment of the support advantage according to the present invention.
Figure 4:
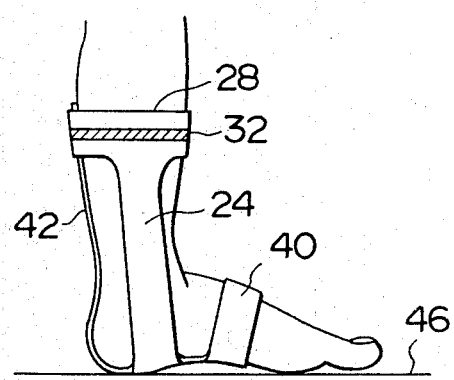
FIG. 4 is a front view showing the fastening procedure of taping.
Figure 5:
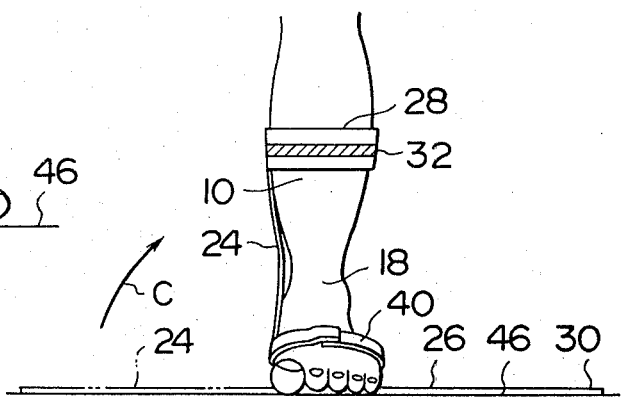
FIGS. 5 and 6 are side views showing the fastening procedure of taping.

As shown in FIG. 3, a support bandage 20 is formed of a thin sheet material punched into a predetermined shape, and it is preferable that the thin sheet material is woven with special tape of yarns in a manner in order to have an extensibility. Furthermore, the aforesaid support bandage 20 is applied to the rear surface thereof with an adhesive, and, as the case may be, a peelable protective film may be further applied onto the adhesive.

The support bandage 20 is shaped in plan view into a shape wherein a transverse 'T' shaped portion is superposed on the center of an 'I' shaped portion as shown in FIG. 3. To state basically, the 'I' shaped portion is to protect an ankle and the 'T' shaped portion to protect an Achilles tendon.

The center of the 'I' shaped portion is formed into a foot sole attachable portion 22, which is connectingly provided at one end thereof with a connecting portion 24 constituting a first extension, and at the other end thereof with an extended portion 26 constituting a second extension, said foot sole attachable portion 22, connecting portion 24 and extended portion 26 being in straight-line forms. Furthermore, the connecting portion 24 and the extended portion 26 are connectingly provided at the forward ends thereof with the intermediate portions of first and second securing portions 28 and 30, respectively. Here, these securing portions 28 and 30 are in parallel to each other and perpendicularly intersect the connecting portion 24 and extended portion 26.

Next, a reference line 32 is drawn in the substantially central portion of the surface of the first securing portion 28 in the longitudinal direction thereof, while, three adjustment lines 34, 36 and 38 being in parallel with the reference line 32 are drawn on the extended portion 26. The distances between the reference and adjustment lines and the center of the foot sole attachable portion are L, L, L and L for the reference line 32 and adjustment lines 34, 36 and 38, respectively, said distances being progressively decreased from L toward L.

Next, the transverse 'T' shaped portion has a 'T' shaped head 40 to be wound around an instep, 'T' shaped leg 42 constitutes a third extension to be attached to an Achilles tendon portion, and a portion adjacent a connection between the 'T' shaped leg 42 and the 'T' shaped head 40 constitutes a foot sole attachable portion 44. In addition, corner portions of this support bandage are provided with proper curvatures, respectively, so as to prevent breakages thereof when tensions are applied to the corner portions. Furthermore, a plurality of tapes in straightline forms may be adhesively attached to one another to form the support bandage 20 formed of an integral, continuous and thin sheet material.

Next, description will hereunder be given of the fastening procedure of this support bandage with reference to FIGS. 4 through 8. Firstly, the support bandage 20 is rested on a floor 46, with the adhesive surface being faced upwardly, and the foot sole 16 is rested on the foot sole attachable portions 22, 44 (Refer to the contour of foot sole indicated by two-dot chain lines in FIG. 3), and the foot sole is adhesively attached thereto.

Subsequently, the 'T' shaped head 40 is wound around the instep, the 'T' shaped leg 32 is adhesively attached to the Achilles tendon portion under a proper tension, and the forward end portion thereof is adhesively attached to the rear portion of the calf 10. Further, the first securing portion 28 is raised along the inner side of the body in a direction indicated by an arrow C in FIG. 5 under a weak tension, and wound around the calf 10. During this winding, the forward end of the 'T' shaped leg 42 is interposed between the first securing portion 28 and the calf 10 and the reference line 32 is adapted to surround the calf 10.

Figure 6:
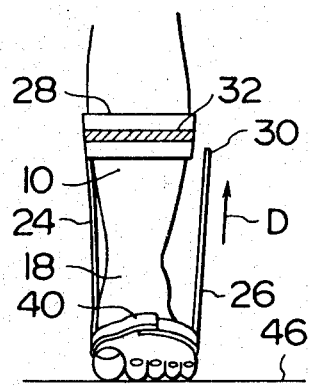
Figure 7:
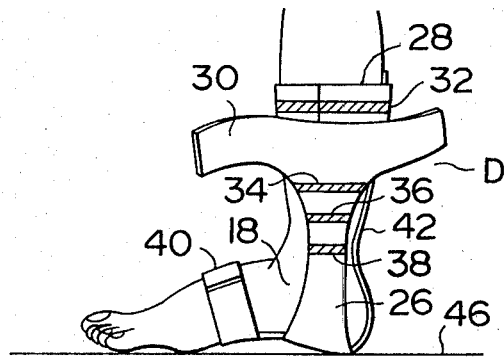
FIGS. 7 and 8 are rear views showing the fastening procedure of taping.
Figure 8:
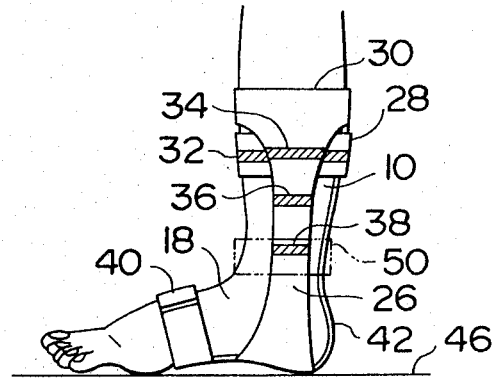

Thereafter, as shown in FIGS. 6 and 7, the second securing portion 30 is raised in the same manner as the first securing portion 28, and further, the extended portion 26 is raised in an extended condition under a high tension as indicated by an arrow D. Simultaneously with this, if the adjustment line 34 is made to coincide with the reference line 32 and the securing portion 30 is wound around the calf 10 to be adhesively attached thereto, then the fastening is completed as shown in FIG. 8.

With the arrangement as described above, the tension of the extended portion 26 makes it possible to prevent the rotation of the ankle 18 toward the inner side of the body to an extreme extent to thereby keep off a sprain of the ankle. And, the 'T' shaped leg 42 makes it possible to prevent the extension of the Achilles tendon to an extreme extent, thus keeping off the damage to the Achilles tendon. Here, the 'T' shaped leg 42 functions not only in protecting the Achilles tendon but also in more reliably protecting the ankle in cooperation with the extended portion 26 than the case where the extended portion 26 is solely used.

In addition, if the tension of the extended portion 26 is to be further increased during the fastening as described above, the adjustment line 36 or 38 may be coincided with the reference line 32. Furthermore, if the extended portion 26 is to be reliably attached to the inner and outer sides of the ankle 18, then a third securing portion 50 indicated by two-dot chain lines in FIG. 3 may be extended to be wound around the ankle as shown in FIG. 8.

Furthermore, combination of the reference line with the adjustment lines is used in determining the extension acting on the extended portion in the abovedescribed embodiment. However, the distances from the foot sole attachable portion to the first and second securing portions may be varied and coincided with each other at the time of fastening so that the proper tension can be determined. Further, the support bandage in the abovedescribed embodiment is usable solely for one leg. However, if this support bandage is to be applied to either right or left leg, then the reference line may be provided on the second securing portion and the adjustment lines on the connecting portion 24.

Figure 9:
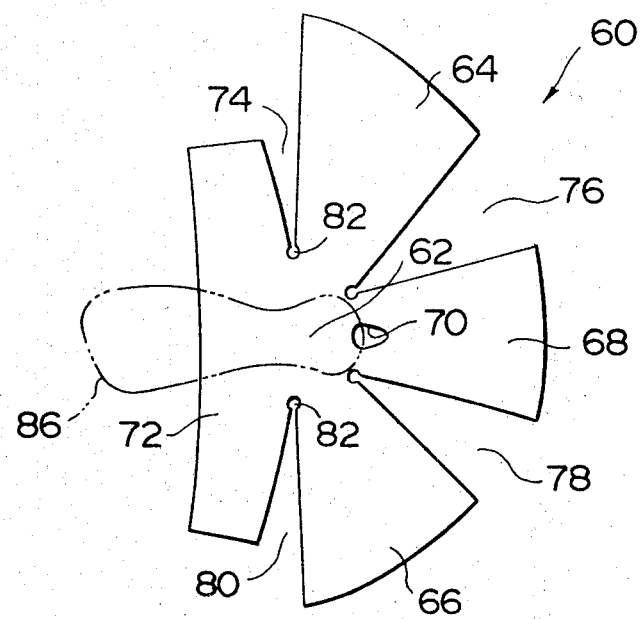
FIG. 9 is a plan view showing a second embodiment of the present invention.
Figure 10:
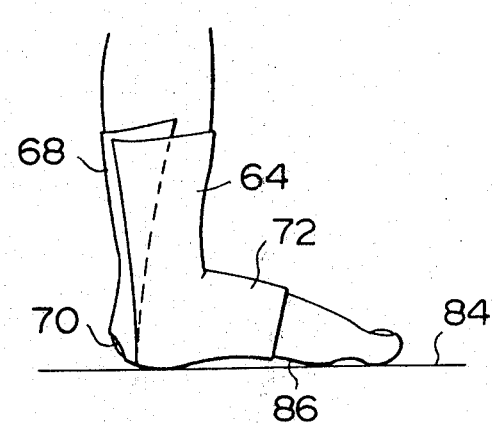
FIG. 10 is a front view showing the fastening procedure of taping.
Figure 11:
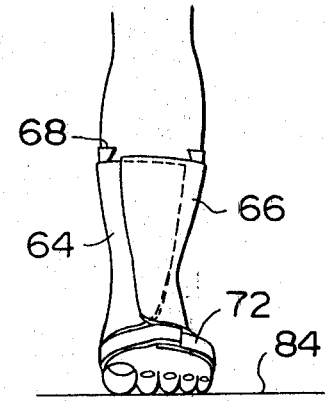
FIG. 11 is a side view showing the fastening procedure of taping.

Description will hereunder be given of a second embodiment of the present invention with reference to FIGS. 9 to 11.

The punched shape of this support bandage 60 is as if a 'K' shape is superposed on a transverse 'T' shape, the central portion of which is a foot sole attachable portion 62, and three extended portions centered about the foot sole attachable portion are radially connected thereto. These extended portions are progressively increased in width toward the forward ends thereof.

A first extended portion 64 is to be closely attached to the inner side of the body, a second extended portion 66 is to be closely attached to the outer side of the body, and both extended portions are extended from the foot sole attachable portion 62 in directions opposite to each other. A third extended portion 68 is to be closely attached to the Achilles tendon portion, interposed at substantially middle position between the first and second extended portions 64 and 66, and an elliptic opening 70 is penetrated at a connecting portion between the foot sole attachable portion 62 and the third extended portion 68.

Contiguously connected to the foot sole attachable portion 62 at the side opposite to the third extended portion 68 is an instep winding portion 72 extending perpendicularly to the third extended portion 68.

This support bandage 60 may be formed by providing four cut-ins 74, 76, 78 and 80 in a thin cloth being substantially semicircular in plan view with the forward ends of the cut-ins ending at circular openings 82 so as not to carelessly expand the respective cut-ins.

Description will hereunder be given of the procedure of fastening this support bandage. Firstly, the support bandage 60 is rested on a floor 84 with an adhesive surface being faced upwardly, the foot sole is rested on the foot sole attachable portion 62 (Refer to the contour of foot sole 68 indicated by two-dot chain lines in FIG. 9), and the foot sole is adhesively attached thereto.

Subsequently, the instep winding portion 72 is wound around the instep, and the third extended portion 68 is adhesively attached to the Achilles tendon portion under a proper tension (See FIG. 10). In this case, the opening 70 provided in the third extended portion 68 contributes to the accommodation of the third extended portion 68 to the curved surface of the heel and prevents wrinkles from occurring. Further, the first extended portion 64 is raised along the inner side of the body under a weak tension, and then, adhesively attached. Thereafter, as shown in FIG. 11, the second extended portion 66 is raised in the same manner as the first extended portion 64, and adhesively attached to the outer side of the body under a tension.

With the arrangement as described above, the tension of the second extended portion 66 makes it possible to prevent the rotation of the ankle toward the inner side of the body to an extreme extent to thereby keep off a sprain of the ankle, and the third extended portion 68 makes it possible to prevent the extension of the Achilles tendon to an extreme extent, thus keeping off the damage to the Achilles tendon.

In addition, in the abovedescribed embodiment, as shown in FIGS. 10 and 11, the extended portions are overlapped each other to cover the ankle leaving no space, so that an extra advantage can be offered in preventing a sprain of the ankle.

Furthermore, the support bandage as described above may be formed of an integral, continuous and thin sheet material in which a plurality of segments are adhesively attached to one another. Further, the adhesive applied onto the rear surfaces of the support bandage is not limited to ones applied to the entire surfaces thereof, but may be ones partially applied to the foot sole attachable portion and the respective extended portions.

With the abovedescribed arrangement, according to the present invention, such outstanding advantages are offered that the operator can fasten the support bandage to himself with no skills required, an accident can be reliably prevented and a high therapentic value can be obtained.

What is claimed is:

1. A support bandage formed of a continuous and thin sheet material with one surface thereof being applied thereto with an adhesive, comprising:
    (a) a foot sole attachable portion;
    (b) a first extended portion to be closely attached to the inner side of the body, which is radially extended from said foot sole attachable portion and the forward end of which is larger in width than the base portion;
    (c) a second extended portion to be closely attached to the outer side of the body, which is radially extended from said foot sole attachable portion and the forward end of which is larger in width than the base portion; and
    (d) a third extended portion to be closely attached to the rear side of the leg, which is radially extended from said foot sole attachable portion which is interposed between said first and second extended portions; whereby said extended portions are adhered to the ankle and therearound, overlapped one another to cover the ankle and thereabout and prevent the rotation of the ankle to an extreme extent.

2. A support bandage as set forth in claim 1, wherein further an instep winding portion is extended from said foot sole attachable portion.

3. A support bandage as set forth in claim 2, wherein said instep winding portion extends perpendicularly to the third extended portion.

4. A support bandage as set forth in claim 4, wherein said first, second and third extended portions are progressively increased in width toward the forward ends thereof.

5. A support bandage as set forth claim 1, wherein said support bandage is formed with four cut-ins to provide extended portions in a thin sheet material being substantially semicircular in plan view.

6. A support bandage as set forth in claim 5, wherein said cut-ins end at a circular opening so as not to extend the respective cut-ins.

7. A support bandage as set forth in claim 1, wherein said support bandage is formed of an integral, continuous cloth material.

8. A support bandage as set forth in claim 1, wherein an elliptical opening contributing to the accommodation of the third extended portion to the curved surface of the heel is penetrated in the vicinity of a connecting portion between the extended portion and the sole attachable portion.

9. A support bandage as set forth in claim 1, wherein a peelable protective film is applied on to said adhesive.

10. A support bandage formed of a continuous cloth material with one side being applied thereto with an adhesive, comprising:
    (a) a foot sole attachable portion;
    (b) a first extended portion to be closely attached to the inner side of the body, which is radially extended from said foot sole attachable portion and the forward end of which is larger in width than the base portion;
    (c) a second extended portion to be closely attached to the outer side of the body, which is radially extended from said foot sole attachable portion and the forward end of which is larger in width than the base portion;
    (d) a third extended portion to be closely attached to the rear side of the leg, which is radially extended from said foot sole attachable portion which is interposed between said first and second extended portions; whereby said extended portions are adhered to the ankle and therearound overlapped one another to cover the ankle and thereabout leaving no space and prevent the rotation of the ankle to an extreme extent; and
    (e) a peelable protective film applied on to said adhesive.

* * * * *